(12) United States Patent
Bal et al.

(10) Patent No.: US 9,409,847 B2
(45) Date of Patent: Aug. 9, 2016

(54) CATALYST FOR SINGLE STEP CONVERSION OF GLYCEROL TO ACRYLIC ACID AND PROCESS FOR THE PREPARATION THEREOF

(71) Applicant: COUNCIL OF SCIENTIFIC & INDUSTRIAL RESEARCH, New Delhi (IN)

(72) Inventors: Rajaram Bal, Dehradun (IN); Bipul Sarkar, Dehradun (IN); Rajib Kumar Singha, Dehradun (IN); Chandrashekar Pendem, Dehradun (IN); Shubhra Acharyya Shankha, Dehradun (IN); Shilpi Ghosh, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 167 days.

(21) Appl. No.: 14/072,916

(22) Filed: Nov. 6, 2013

(65) Prior Publication Data

US 2014/0128632 A1    May 8, 2014

(30) Foreign Application Priority Data

Nov. 7, 2012 (IN) .......... 3442/DEL/2012

(51) Int. Cl.
| | | |
|---|---|---|
| *B01J 23/889* | (2006.01) |
| *B01J 35/00* | (2006.01) |
| *B01J 37/00* | (2006.01) |
| *C07C 51/285* | (2006.01) |
| *B01J 37/03* | (2006.01) |
| *B01J 37/10* | (2006.01) |

(52) U.S. Cl.
CPC .......... *C07C 51/285* (2013.01); *B01J 23/8892* (2013.01); *B01J 35/002* (2013.01); *B01J 37/0018* (2013.01); *B01J 37/031* (2013.01); *B01J 37/10* (2013.01)

(58) Field of Classification Search
CPC .. B01J 23/8892; B01J 35/002; B01J 37/0018; B01J 37/031; B01J 37/10; C07C 51/285
See application file for complete search history.

(56) References Cited

U.S. PATENT DOCUMENTS 7,910,771 B2    3/2011  Dubois et al.

FOREIGN PATENT DOCUMENTS

EP    1 710 227 A1    10/2006

OTHER PUBLICATIONS

Cleveland, Cutler J. Morris, Christopher. (2006). Dictionary of Energy. Elsevier.*
Soriano, M.D. et al., Tungsten-Vanadium mixed oxides for the oxidehydration of glycerol into acrylic acid, Green Chemistry, 2011, vol. 13, pp. 2954-2962.
Wang, F., et al., Catalytic dehydration of glycerol over vanadium phosphate oxides in the presence of molecular oxygen, Journal of Catalysis, 268, 2009, pp. 260-267.
Deleplanque, J., et al., Production of acrolein and acrylic acid through dehydration and oxydehydration of glycerol with mixed oxide catalysts, Catalysis Today, 157, 2010, pp. 351-358.

* cited by examiner

*Primary Examiner* — Paul A Zucker
*Assistant Examiner* — Mark Luderer
(74) *Attorney, Agent, or Firm* — Hudak, Shunk & Farine Co., LPA

(57) ABSTRACT

The present invention provides a process and a solid catalyst for oxydehydration of glycerol to acrylic acid with $H_2O_2$ under mild experimental condition at atmospheric pressure. The process provides a single step liquid phase selective oxidation glycerol to acrylic acid over nanocrystalline Cu supported $\alpha$-$MnO_2$ catalyst. The process provides glycerol conversion of 20-78% and selectivity of acrylic acid up to 86%.

8 Claims, 2 Drawing Sheets

A = low magnification; B = high magnification

CATALYST FOR SINGLE STEP CONVERSION OF GLYCEROL TO ACRYLIC ACID AND PROCESS FOR THE PREPARATION THEREOF

FIELD OF THE INVENTION

The present invention relates to catalyst for the liquid phase oxydehydration of glycerol to acrylic acid with hydrogen peroxide as oxidant for the production of acrylic acid and process for the preparation of the catalyst. Particularly, the present invention relates to a process for the single step conversion of glycerol to acrylic acid over nanocrystalline Cu supported α-$MnO_2$ catalyst. More particularly, the present invention relates to a process for the liquid phase conversion of glycerol to acrylic acid by using a single Cu—Mn catalyst with hydrogen peroxide as oxidant.

BACKGROUND OF THE INVENTION

As the dependency on fossil fuel are increasing constantly, new formula is modified from the Klaus model and thus assumes a continuous compound rate and computes fossil fuel reserve depletion times for oil, coal and gas of approximately 35, 107 and 37 years, respectively. On this situation researcher are trying to develop new ways to utilize renewable resources as the feedstock for the generation of energy and production of chemical toward negative $CO_2$ emission and fossil fuel dependency.

Innovations in renewable energy generation e.g. biodiesel are taking the spotlight of new generation. The sharp rise in world biodiesel production has created a glut of glycerol, by-product of saponification or the process of soap making and transesterification or the production of biodiesel. In order to improvise the biofuel economy and put this waste stream to good use new catalytic route must be found. Glycerol can be accounted for 10% of the by-products of biodiesel production. Since for each gallon of biodiesel produces approximately 0.75 lb of glycerol, so this would be a very practical to use glycerol for production of fine chemicals or clean fuel such as hydrogen. To meet the commercial target the oxydehydration of glycerol is one of the most promising options to be focused.

Acrylic acid is one of the most important chemical largely employed by the chemical industry for the production of super absorber, polymer, adhesive, paint, plastic & rubber synthesis, detergent etc. Various catalyst has been targeted for selectively converting glycerol to acrolein, among the supports with Lewis acidity such as α-$Al_2O_3$, $SiO_2$ and $TiO_2$ are been applied but the results are not satisfactory. However, metal oxide of 2nd and 3rd transition series e.g. $Nb_2O_5$, $WO_3/ZrO_2$ metal phosphates, SAPO's and zeolite are shown quite appreciable selectivity of acrolein. As a general rule, the hydration reaction is favoured at low temperatures, and the dehydration reaction is solution of glycerol was favoured at high temperatures therefore to obtain acrolein, it is necessary to use a sufficient temperature, and/or forward flow to shift the reaction. The reaction may be performed in the liquid phase or in the gas phase; perhaps this type of reaction is known to be catalysed by acids. Production of acrylic acid by direct dehydration followed by oxidation of glycerol takes place by a two-step reaction pathway which involves the formation of acrolein as an intermediate on the appropriate metal catalyst (such as W, Cu, Mn) and finally the oxidation of acrolein to acrylic acid.

Reference may be made to European patent EP 1710227B1, claimed a two-step process which includes dehydration of (~50 wt %) aqueous solution of glycerol over alumina base catalyst impregnated with phosphoric acid & silica followed by oxidation step over alumina supported Mo—V—W—Cu—O mixed oxide. The process gives acrylic acid yield of 55 to 65%.

Reference may be made to U.S. Pat. No. 7,910,771, the prospective of single step conversion of acrylic acids from glycerol was calmed by Jean-Luc Dubois, Millery, where a single oxydehydration step of glycerol to acrylic acid was described in presence of molecular oxygen, 10-50 wt % of aqueous solution of glycerol was passed over a plate exchanger at 250° C. to 350° C.

Reference may be made to article in the Green Chemistry, 2011, 13, 2954-2962 by F. Cavani et al. where they reports a one pot transformation of glycerol to acrylic acid with a Vanadium incorporated $WO_3$ catalyst. Under the process condition only 25% yield of acrylic acid was obtained at 280° C. Moreover, the catalyst progressively generate surface $V^{+5}$ species, which resides in the hexagonal bronze structure of the catalyst, led to a decrease in the selectivity to acrylic acid and to the concomitant rise in carbon oxide formation.

Reference may be made to article in the Journal of Catalysis, 2009, 2, 260-267, in which Ueda et al. and his group reported dehydration of glycerol over vanadium phosphate oxide (VPO) in a gas phase fixed bed reactor at a temperature range of 250° C. to 350° C. At about 300° C. they found 100% glycerol conversion with 3% acrylic acid over $VOHPO_4.0.5H_2O$. With the increment of $O_2/N_2$ ratio to 6/18 the acrylic acid formation goes up to 7%, whereas when the reaction temperature rises to 350° C. the acrylic acid conversion goes to the highest of 8%.

Reference may be made to article in the Catalysis Today, 2010, 157, 351-358 in which Japanese worker Ueda and his group reported the production of acroline and acrylic acid through dehydration and oxydehydration of glycerol with mixed FeP—H catalysts. They achieved almost 100% glycerol conversion with 1.2% acrylic acid at 180° C. with a GHSV of 550 $h^{-1}$.

The drawback of the processes reported so far is that all of those processes either possess low production of acrylic acid or involve multiple step process under pressurized reaction condition. In the multistep approach it was in evidence that the overall transformation includes a dehydration step to convert glycerol to acrolein which requiring adequate acidity followed by an oxidation step into acrylic acid. To overcome that boundation many researchers trying to develop a new process with a single step catalyst which can selective convert glycerol to acrylic acid in a mild reaction condition. The use of a single bi-functional catalyst aims to meet the challenge for the development of new catalytic approaches to convert glycerol into acrylic acid with a single catalyst.

OBJECTIVES OF THE INVENTION

The main object of the present invention is to provide a single step oxydehydration process to convert glycerol to acrylic acid over nanocrystalline Cu—Mn solid catalyst.

Another object of the present invention is to provide a process, which selectively gives acrylic acid from glycerol under mild condition.

Yet another object of the present invention is to provide a process and catalyst which uses by-product of bio-diesel (glycerol) for future fuel alternatives.

Yet another object of the present invention is to provide a process which works in liquid phase condition without any leaching for the production of acrylic acid from glycerol.

Yet another object of the present invention is to provide a Cu—Mn catalyst and which can be prepared easily to produce acrylic acid from glycerol.

SUMMARY OF THE INVENTION

Accordingly, present invention provides a nanocrystalline Cu supported α-$MnO_2$ catalyst comprising Cu in the range of 1 to 5 (wt %) $MnO_2$ in the range of 99 to 95 (wt %) having particle size in the range of 25 to 50 nm.

In an embodiment of the present invention, nanocrystalline Cu supported α-$MnO_2$ catalyst is useful for single step conversion of glycerol to acrylic acid.

In an embodiment, present invention provide an improved process for the preparation of nanocrystalline Cu supported α-$MnO_2$ catalyst as claimed in claim 1 and the said process comprising the steps of:
  a. mixing of $Cu(NO_3)_2.3H_2O$ and $Mn(NO_3)_2.3H_2O$ solution at temperature ranging between 35 to 80° C., where the weight ratio of Cu to Mn ranges between 0.5 to 15;
  b. adding a surfactant solution drop wise into the solution as obtained in step (a) with constant stirring, where the molar ratio of Cu to surfactant ranges between 0.005 to 0.1;
  c. adding of reducing agent drop wise into the solution as obtained in step (b) with constant stirring to get a gel where the molar ratio of Cu to reducing agent ranges between 0.5 to 1.5;
  d. heating the gel as obtained in step (c) at temperature in the range of 100 to 200° C. hydrothermally for a period ranging between 12 to 30 hours to obtain solid followed by washing the solid with excess water;
  e. drying the solid as obtained in step (d) at temperature in the range of 80 to 110° C. for a period ranging between 6-12 h;
  f. calcining the solid as obtained in step (e) at temperature ranging between 300 to 800° C. for a period of 6 to 12 hr to obtain nanocrystalline Cu supported α-$MnO_2$ catalyst.

In another embodiment of the present invention, surfactant used in step (b) is cetyltrimethyl ammonium bromide (CTAB).

In yet another embodiment of the present invention, reducing agent used in step (c) is hydrazine.

In yet another embodiment, present invention provides a process for single step conversion of glycerol to acrylic acid using catalyst as claimed in claim 1, wherein the said process comprising the steps of:
  i. mixing nanocrystalline Cu supported α-$MnO_2$ catalyst with Cu to α-$MnO_2$ weight ratio present in the range of 0.5 to 20%, solvent and glycerol followed by adding $H_2O_2$ with weight ratio of glycerol to catalyst is in the range of 20 to 200, with molar ratio of glycerol to $H_2O_2$ in the range of 1:2 to 1:15 at temperature in the range of 60 to 120° C., while agitating the reaction mixture, for a period in the range of 1 to 30 hr, followed by cooling to at temperature in the range of 25 to 30° C. to obtain acrylic acid.

In yet another embodiment of the present invention, the molar ratio of substrate to $H_2O_2$ is preferably in the range 1:2.5 to 1:10.

In yet another embodiment of the present invention, the weight ratio of glycerol to catalyst is preferably in the range of 5 to 20.

In yet another embodiment of the present invention, the conversion of glycerol to acrylic acid in the range of 20-78%.

In yet another embodiment of the present invention, the selectivity of the acrylic acid is in the range of 20 to 84%.

DETAILED DESCRIPTION OF THE INVENTION

The present invention provides a process for the preparation of nanocrystalline Cu—$MnO_2$ by hydrothermal synthesis method for the selective single step oxidation of glycerol to acrylic acid in the liquid phase reaction using hydrogen peroxide as an oxidant involves the following steps:

Preparation of the gel composition using $Cu(NO_3)_2.3H_2O$, $Mn(NO_3)_2.9H_2O$, Cetyltrimethylammonium bromide (CTAB), Hydrazine, $H_2O$ where $Cu(NO_3)_2.3H_2O$ and $Mn(NO_3)_2.9H_2O$ are the precursors for Cu and Mn respectively.

The weight ratio of Cu to $MnO_2$ varied in the range of 0.05 to 20

The mole ratio of Cu to CTAB varied in the range of 0.75 to 1.5

The pH of the mixture was varied in the range of 9 to 10 by the drop wise addition of aqueous ammonia.

The mole ratio of Cu to hydrazine varied in the range of 0.75 to 1.5

The mixing gel was transferred in a Teflon lined autoclave and kept in an oven with temperature range of 150 to 200° C. for 20-30 h.

The product was filterer with excess water and dried in an oven with temperature range of 100 to 120° C. The dried product was calcined in a furnace in the temperature range of 400-800° C.

Liquid phase selective oxidation reaction was carried out in a two neck Round Bottom flask containing 0.1 g catalyst, 10 ml of solvent and 1 g substrate to which 1 ml $H_2O_2$ was added. Then the reaction mixture was stirred at 90° C. for several hours. After completion of the reaction, the reaction mixture was cooled in cold water to room temperature and analyzed by GC fitted with a capillary column and FID detector.

EXAMPLES

The following examples are given by way of illustration and therefore should not be construed to limit the scope of the present invention.

Example 1

In the typical synthesis procedure adequate amount of $Cu(NO_3)_2.2.5H_2O$ (98%, Aldrich) was dissolved in 4 ml $H_2O$ along with 5.77 g $Mn(NO_3).4H_2O$ (98%, Aldrich). After the solvation, 1:1 copper to CTAB where added and stirred until a homogeneous solution was obtained. The pH of the mixture was maintained at 9 by the drop wise addition of aqueous ammonia, to the obtained slurry, 1:1 hydrazine was added in respect to Cu. Finally the homogeneous slurry was transferred into an autoclaved for hydrothermal treatment at 180° C. for 24 hrs. The obtained product was washed and dried followed by calcination in static air for 6 h.

Figure 1:
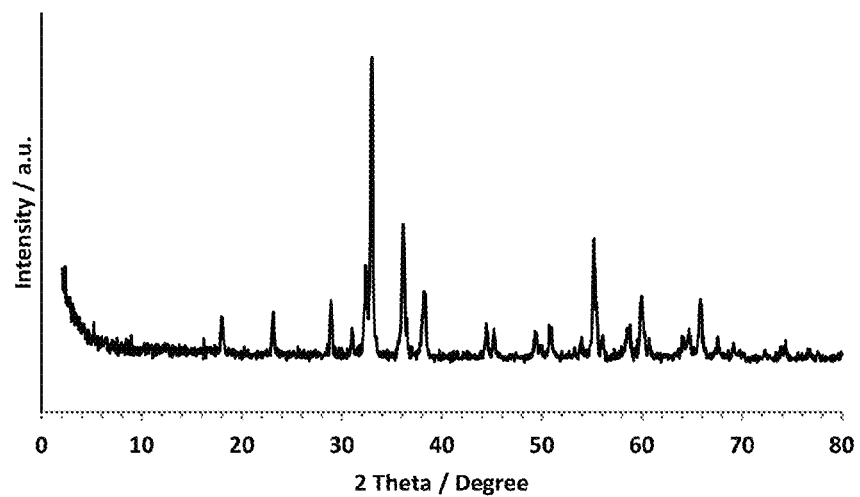
FIG. 1 represents XRD of the prepared catalyst.
Figure 2:
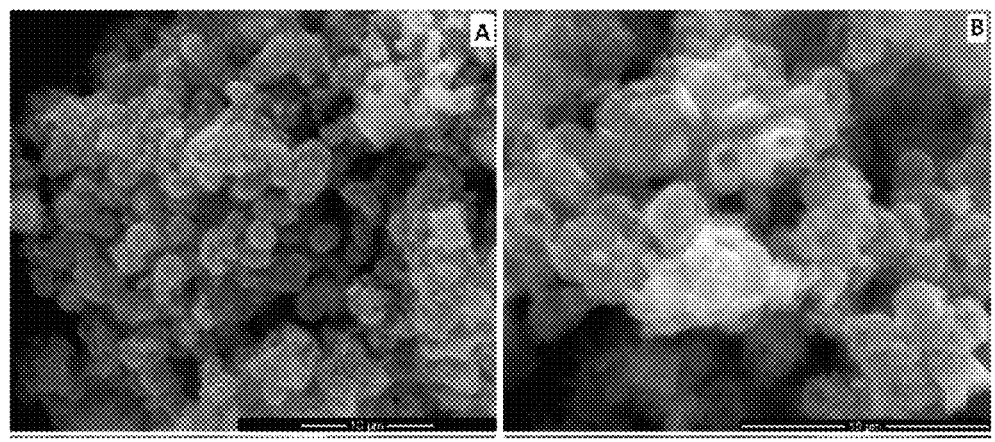
FIG. 2 represents SEM images of the Cu—$MnO_2$ catalyst.
Figure 3:
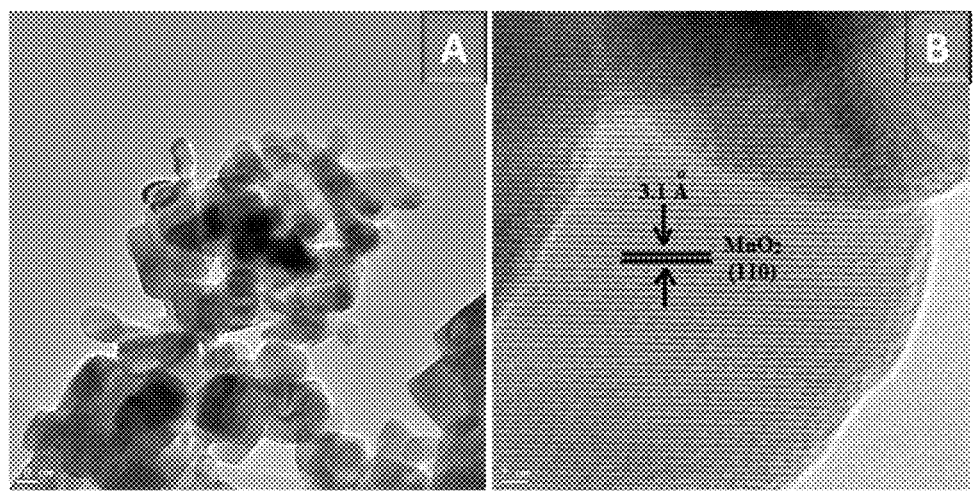
FIG. 3 represents TEM images of the Cu—MnO2 catalyst.

XRD, SEM and TEM images of the catalyst are given in FIGS. 1, 2 and 3 respectively.

Example-2

This example describes the production of acrylic acid form glycerol in liquid phase with $H_2O_2$ as oxidant over $Cu$—$MnO_2$ solid catalyst.

Oxidation of glycerol was carried out in a two neck Round Bottom flask containing 0.1 g catalyst, 10 ml of solvent and 1 g substrate to which 1 ml $H_2O_2$ was added. Then the reaction mixture was stirred at 90° C. for 30 hours. On completion, the reaction mixture was cooled to ~30° C. (room temperature) and analysed by a Thermo GC equipped with a FID.

Process Conditions
Catalyst: 0.02 g
$Cu:MnO_2$ weight ratio in the catalyst=5:95.
Reaction temperature: 90° C.
Reaction time: 20 h
Product Analysis
Glycerol conversion: 77.1%
Acrylic acid: 74.7%

Example-3

The example describes the effect of temperature on production of acrylic acid form glycerol in liquid phase with $H_2O_2$ as oxidant over $Cu$—$MnO_2$ solid catalyst. The product analysis presented in Table-1.

Process Conditions
Catalyst: 0.02 g
$Cu:MnO_2$ weight ratio in the catalyst=5:95.
Reaction time: 20 h
Product analysis

TABLE 1

| Temperature (° C.) | Conversion (%) Glycerol | Selectivity (%) Acrylic acid |
|---|---|---|
| 60 | 71.1 | 73.9 |
| 90 | 77.1 | 74.7 |
| 120 | 77.9 | 62.7 |

Example-4

The example describes the effect of time on production of acrylic acid form glycerol over $Cu$—$MnO_2$ solid catalyst. The product analysis presented in Table 2

Process Conditions
Catalyst: 0.02 g
$Cu:MnO_2$ weight ratio in the catalyst=5:95.
Reaction temperature: 90° C.
Product analysis

TABLE 2

| Time (h) | Conversion (%) Glycerol | Selectivity (%) Acrylic acid |
|---|---|---|
| 6 | 64.6 | 61.2 |
| 10 | 70.5 | 66.3 |
| 20 | 77.1 | 74.7 |
| 30 | 81.9 | 81.2 |

Example-5

The example describes the effect of glycerol to oxidant ($H_2O_2$) ratio in terms of glycerol conversion and acrylic acid selectivity over $Cu$—$MnO_2$ catalyst. The product analysis presented in Table-3.

Process Conditions
Catalyst: 0.02 g
$Cu:MnO_2$ weight ratio in the catalyst=5:95.
Reaction temperature: 90° C.
Reaction time: 20 h

TABLE 3

| Glycerol:$H_2O_2$ (mole ratio) | Conversion (%) Glycerol | Selectivity (%) Acrylic acid |
|---|---|---|
| 1:2.5 | 49.9 | 73.6 |
| 1:5 | 77.1 | 74.7 |
| 1:7.5 | 75.6 | 77.7 |
| 1:10 | 70.1 | 78.5 |

ADVANTAGES OF THE INVENTION

1. The process of the present invention prepares a catalyst $Cu$—$MnO_2$ by hydrothermal synthesis method in presence of surfactant for the selective oxidation of glycerol to acrylic acid reaction.
2. The process of the present invention is to convert glycerol in to fine chemicals such as acrylic acid in a single step with a single solid catalyst.
3. The process provides not only good conversion but also good acrylic acid selectivity.
4. The process utilizes glycerol (by-product of saponification or the process of soap making and transesterification or the production of biodiesel) to produce acrylic acid, which become the major advantages of this process.
5. The catalyst shows no deactivation and no leaching up to 4 reuse at 90° C.
6. The catalyst is used in very low amounts to obtain very high conversion and acrylic acid selectivity.

We claim:
1. Nanocrystalline Cu supported α-$MnO_2$ catalyst comprising Cu in the range of 1 to 5 (wt %) $MnO_2$ in the range of 99 to 95 (wt %) having a particle size in the range of 25 to 50 nm.
2. A process for the preparation of a nanocrystalline Cu supported α-$MnO_2$ catalyst as claimed in claim 1, said process comprising the steps of:
    a. mixing $Cu(NO_3)_2.3H_2O$ and $Mn(NO_3)_2.3H_2O$ solutions at temperature ranging between 35 to 80° C.;
    b. adding a surfactant solution into the solution as obtained in step (a) with stirring, where the molar ratio of elemental Cu to surfactant ranges between 0.005 to 0.1;
    c. adding a reducing agent into the solution as obtained in step (b) with stirring to form a gel, where the molar ratio of Cu to reducing agent ranges between 0.5 to 1.5;
    d. heating the gel as obtained in step (c) at a temperature in the range of 100 to 200° C. for a period ranging between 12 to 30 hours to obtain a solid followed by washing the solid with water;
    e. drying the solid as obtained in step (d) at a temperature in the range of 80 to 110° C. for a period ranging between 6-12 hr; and
    f. calcining the solid as obtained in step (e) at a temperature ranging between 300 to 800° C. for a period of 6 to 12 hr to obtain the nanocrystalline Cu supported α-$MnO_2$ catalyst.
3. The process as claimed in claim 2, wherein the surfactant used in step (b) is cetyltrimethyl ammonium bromide (CTAB).

4. The process as claimed in claim 2, wherein the reducing agent used in step (c) is hydrazine.

5. A process for a single step conversion of glycerol to acrylic acid using a nanocrystalline Cu supported $\alpha$-$MnO_2$ catalyst having a particle size of from 25 to 50 nm; wherein said process comprising the steps of:

mixing said nanocrystalline Cu supported $\alpha$-$MnO_2$ catalyst with an elemental Cu to $\alpha$-$MnO_2$ weight ratio in the range of 0.5 to 5%, solvent and glycerol followed by adding $H_2O_2$ with a weight ratio of glycerol to catalyst being in the range of 20 to 200, with a molar ratio of glycerol to $H_2O_2$ being the range of 1:2 to 1:15, at a temperature in the range of 60 to 120° C., while agitating the reaction mixture for 1 to 30 hr, followed by cooling to a temperature in the range of 25 to 30° C. to obtain acrylic acid.

6. The process as claimed in claim 5, wherein the molar ratio of elemental Cu to $H_2O_2$ is in the range of 1:2.5 to 1:10.

7. The process as claimed in claim 5, wherein the conversion of glycerol to acrylic acid in the range of 20 to 78 mole %.

8. The process as claimed in claim 5, wherein the selectivity of the acrylic acid is in the range of 20 to 84 mole %.

\* \* \* \* \*